United States Patent [19]

Kimura

[11] 4,423,436

[45] Dec. 27, 1983

[54] IMAGE PICKUP APPARATUS

[75] Inventor: Kenji Kimura, Tachikawa, Japan

[73] Assignee: Olympus Optical Co., Ltd., Tokyo, Japan

[21] Appl. No.: 260,299

[22] Filed: May 4, 1981

[30] Foreign Application Priority Data

May 9, 1980 [JP] Japan .................................. 55-61347

[51] Int. Cl.³ .............................................. H04N 5/19
[52] U.S. Cl. ..................................... 358/98; 358/211; 358/228
[58] Field of Search ................. 358/211, 219, 93, 106, 358/98, 282, 214, 95, 99, 111, 228, 221; 235/455; 250/205

[56] References Cited

U.S. PATENT DOCUMENTS

| | | | |
|---|---|---|---|
| 3,555,181 | 1/1971 | Thommen | 358/228 |
| 3,602,641 | 8/1971 | Heise | 358/111 |
| 3,678,190 | 7/1972 | Cook | 178/6.8 |
| 3,835,247 | 9/1974 | Soames | 358/219 |
| 3,918,028 | 11/1975 | Humphrey et al. | 235/472 |
| 3,944,979 | 3/1976 | Kwok | 340/146.3 AG |
| 4,158,859 | 6/1979 | Kerbel | 358/228 |

FOREIGN PATENT DOCUMENTS 51-26719 7/1976 Japan .
1308047 2/1973 United Kingdom .

Primary Examiner—Joseph A. Orsino, Jr.
Attorney, Agent, or Firm—Frishauf, Holtz, Goodman and Woodward

[57] ABSTRACT

An image pickup apparatus having a light source for providing an illumination light; an endoscope including illumination fiber optics for transmitting the illumination light to a foreground subject, and image fiber optics for sensing an optical image of the subject and transmitting this image; a video circuit for converting the optical image into a video signal; and a feedback circuit for converting the video signal into a light source drive signal and for continuously feeding the light source drive signal back to continuously set the light source so that the video signal is maintained at a substantially constant prescribed level.

The light source, illumination fiber, optics image fiber, optics video circuit and feedback circuit jointly constitute an automatic level control loop which is continuously actuated as to continuously set the video signal to the substantially constant prescribed level.

5 Claims, 6 Drawing Figures

IMAGE PICKUP APPARATUS

BACKGROUND OF THE INVENTION

This invention relates to an image pickup device coupled to, for example, a prescribed optical image transmission device to produce predetermined video signals, and more particularly to a television camera apparatus jointly used with a fiberscope to carry out a particular function such as an iris servo control.

As used herein, the term "iris servo function" is defined to mean a function of generating a video signal always having a prescribed voltage level, regardless of the brightness of a foreground subject whose image is to be picked up. This iris servo function fundamentally corresponds to the electric eye (EE) mechanism of the ordinary camera. The iris servo device of the conventional television camera generally comprises the undermentioned servo system. Namely, the conventional iris servo device detects the average voltage level or peak level of video signals obtained from a television camera. The iris mechanism of the television camera is servo-controlled in accordance with the result of said detection, thereby controlling the brightness of a foreground subject entering the target plane of the image pickup device of the television camera to a fixed level.

Hitherto, an automatic gain control (AGC) circuit has been used as means for electrically fixing the voltage level of the aforesaid video signal. Another known process of controlling the voltage of the video signal to a fixed level comprises the joint use of the AGC circuit and the aforementioned mechanical servo device. In this case, however, the mechanical servo device and AGC circuit are actuated independently of each other. In other words, while the mechanical servo loop is operated, the electric servo loop (AGC circuit) does not work. Conversely where the electric servo loop (AGC circuit) is operated, the mechanical servo loop becomes inoperative. The reason for the application of this procedure is that the independent actuation of the two servo loops enables a stable, accurate servo function to be more easily realized. It is known that a foreground subject whose image is projected on the image pickup device is preferred to have as great a brightness as a video signal-processing circuit is not saturated. The reason for this is that the greater the brightness of light entering the image pickup device, the higher the voltage level of a signal supplied to the video signal-processing circuit with the corresponding improvement in the signal to noise (S/N) ratio.

However, with the conventional image pickup device provided with an iris servo system consisting of the mechanical servo loop and electric servo loop, it is necessary for the operator to unfailingly determine a timing in which the operation of said two servo loops should be changed over in order to obtain a large S/N ratio over a broad range of the brightness of a foreground subject. However, this requirement demands the television camera operator to carry out a time-consuming and initiating changeover operation.

SUMMARY OF THE INVENTION

This invention has been accomplished in view of the above-mentioned circumstances, and is intended to provide an image pickup apparatus which can unfailingly follow broad range changes in the brightness of a foreground subject with a high S/N ratio retained.

To attain the above-mentioned object, this invention provides an impage pickup apparatus which comprises:

light source means for providing an illumination light;

illumination means coupled to said light source means for transmitting the illumination light to a foreground subject to be illuminated;

image transmission means for sensing an optical image of the foreground subject illuminated by said illumination means and transmitting the optical image;

the illumination means and image transmission means being part of an endoscope;

image signal conversion means coupled to said image transmission means for converting the optical image into a video signal; and feedback means coupled to said light source means and image pickup means for converting the video signal into a light source drive signal and feeding said light source drive signal back to said light source means, and wherein said light source means, illumination means, image transmission means, image signal conversion means and feedback means jointly constitute an automatic level control loop which is continuously actuated as to continuously set the amount of illumination light to cause the video signal to be at a substantially constant prescribed level.

A television camera provided with an iris servo function embodying this invention makes it unnecessary to manually change over the operation of the mechanical and electric servo loops, thereby enabling the operator to devote his attention to the photographing of a foreground subject. Further, with the television camera of the invention, the luminance of a light source can be varied over a broad range in accordance with the brightness of a foreground subject, enabling the image pickup means always to receive an optical image having a sufficient brightness, and consequently assuring the production of a video signal having a high S/N ratio.

DETAILED DESCRIPTION OF THE PREFERRED EMBODIMENT

Description is now given with reference to the accompanying drawings of an image pickup apparatus embodying this invention. Throughout the drawings, the same or similar parts are denoted by the same or similar numerals, repeated description thereof being omitted for briefness.

Figure 1:
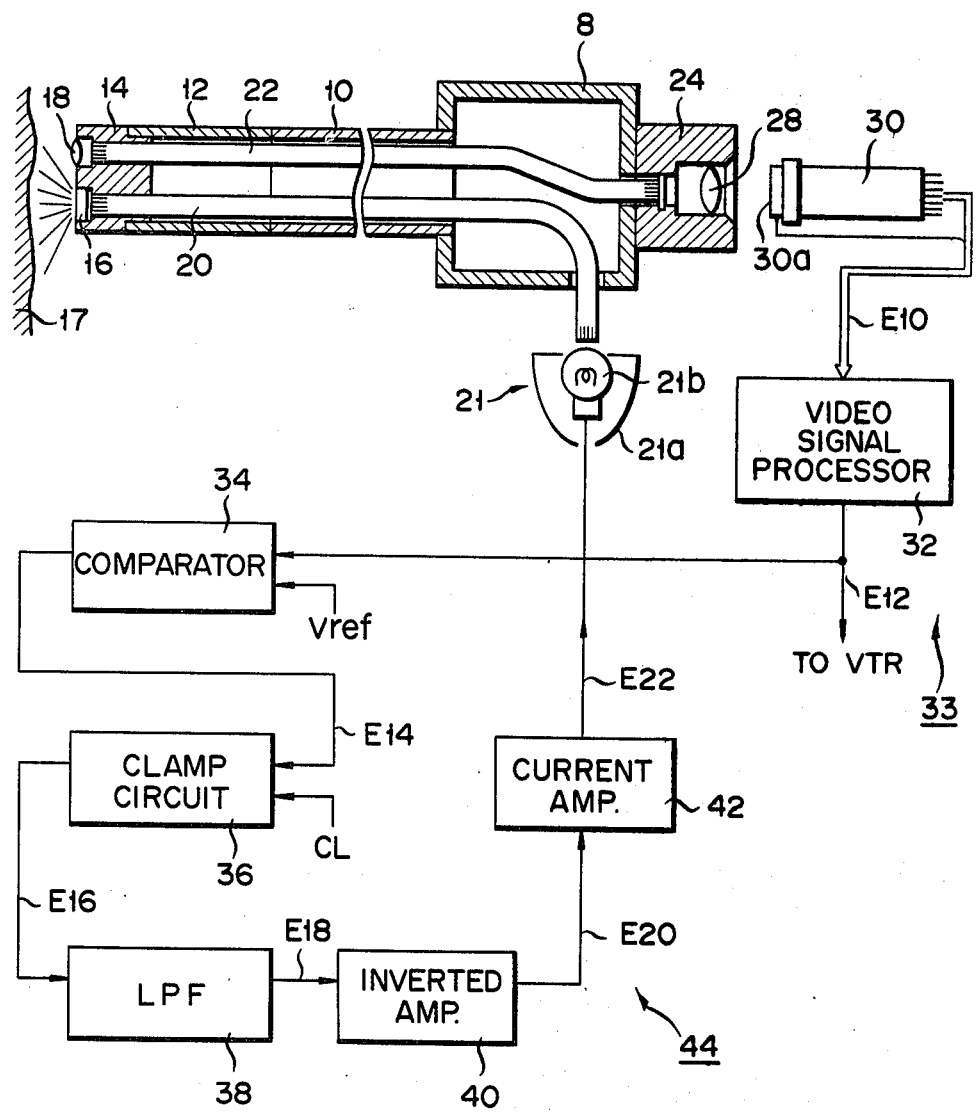
FIG. 1 shows the arrangement of an image pickup apparatus embodying this invention.

Description is given with reference to FIG. 1 of a fiberscope used as an endoscope. A flexible tube 10 is connected to a control section 8 of the endoscope. The flexible tube 10 is connected to a distal end portion 14 by means of a bending section 12. The tip of the distal end portion 14 is fitted with a light guide 16 and also an object lens 18 included in an observation optical system. The light guide 16 is connected to a light source 21 by means of a light guide fiber bundle 20. The light source 21 is formed of a white light lamp 21b provided with a reflector 21a. The object lens 18 is connected to an eyepiece section 24 by means of an image guide fiber bundle 22. An optical system 28 and image pickup tube 30 are concentrically arranged with the optical axis of the proximal end of the image guide fiber bundle 22 fixed to the eyepiece section 24.

The light source 21 supplies an illumination light to the light guide fiber bundle 20 acting as illumination means for projecting an illumination light on a foreground subject 17. The image guide fiber bundle 22 acts as image transmission means for conducting the optical image of the foreground subject 17 to the image pickup tube 30.

The image pickup tube 30 may be formed of a vidicon or CCD image sensor element. A distance between a target plane 30a of the image pickup tube 30 and the optical system 38 is so adjusted as to cause the optical image of the foreground subject 17 to be accurately focused on the target plane 30a. This focus adjustment can be effected by a focus control apparatus disclosed in Japanese patent application Nos. 58,399/80 or 79,742/80.

An output video signal E10 from the image pickup tube 30 is supplied to a video signal-processing circuit 32, which in turn processes said output video signal E10 as prescribed and sends forth a video signal E12 adapted for the ordinary television system. For detailed information on said video signal-processing circuit 32, reference is made to "ITV camera" published by the Japan Broadcasting Publication Association. The image pickup tube 30 and video signal-processing circuit 32 (or the type combined with a focus control device) jointly constitute image pickup means 33 for converting the optical image of the foreground subject 17 transmitted by the image guide fiber bundle 22 into a video signal E12.

Figure 2:
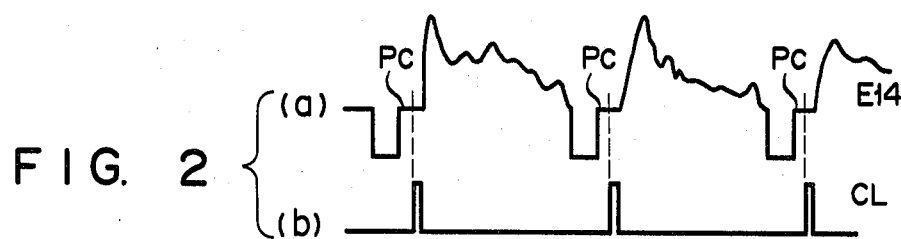
FIG. 2 is a waveform diagram illustrating the manner in which DC restoration is carried out in the image pickup apparatus of FIG. 1.

The video signal E12 is supplied to, for example, a recording device (VTR) or monitor TV device, and also to a comparator 34. The comparator 34 compares the potential of the video signal E12 with a reference potential $V_{ref}$, and sends forth a first signal E14 corresponding to a difference between both potentials. The first signal E14 is conducted to a clamp circuit 36. At this time a level approaching the block portion of the first signal E14 is clamped in the clamp circuit 36 when a clamp pulse CL is issued. As a result, the D.C. component of the first signal E14 is restored. The clamp pulse CL is sent forth in synchronism with a horizontal synchronization signal included in the video signal E12. FIGS. 2a and 2b show waveforms illustrating the manner in which the above-mentioned D.C. component of the first signal E14 is restored. FIGS. 2a and 2b indicate that where the clamp pulse CL is issued, the D.C. level of the first signal E14 at a prescribed point $P_c$ is clamped. A second signal E16 corresponding to the D.C. component thus restored is supplied to a low pass filter (LPF) 38. A third signal E18 which has been fully stripped of ripple components by the LPF 38 is amplified by an inverted amplifier 40 into a fourth signal E20. In the arrangement of FIG. 1, the third signal E18 corresponds to the average of the second signal E16. The fourth signal E20 is amplified by a current amplifier 42 into a light source drive signal E22 having a sufficient amount of energy. This light source drive signal E22 is supplied to the lamp 21b of light source 21. The elements 34 to 42 jointly constitute feedback means 44 which converts the video signal E12 into the light source device signal E22 and feeds said light source drive signal E22 back to the light source 21.

The light source 21, light guide fiber bundle 20, image guide fiber bundle 22, image pickup means 33 and feedback means 44 jointly constitute an automatic level control loop so actuated as to cause the voltage of the video signal E12 to be set at such a prescribed level as corresponds to the reference potential $V_{ref}$. Now let it be assumed that the light guide 16 is so spaced from the foreground subject 17 as to cause only a dark light to be projected on the target plane 30a of the image pickup tube 30. In this case the video signal E12 is decreased in voltage level to reduce a difference between the potential of said signal E12 and the reference potential $V_{ref}$, causing the first signal E14 to fall in voltage level, with a rise in the voltage level of the light source drive signal E22. As a result, the lamp 21b gets brighter, enabling a larger amount of light to be supplied to the foreground subject 17. Therefore, a brighter light is projected on the target plane 30a of the image pickup tube 30 with a rise in the voltage level of the video signal E12. Conversely where a brighter light is projected on the target plane 30a, then a difference between the potential of the video signal E12 and reference potential $V_{ref}$ increases to cause the lamp 21b to get darker to the corresponding extent. The above-mentioned automatic voltage level control operation is carried out in such a manner as minimizes the absolute value of a difference between the potential of the video signal E12 and reference potential $V_{ref}$.

The extent to which the voltage level of the video signal E12 is controlled by the aforesaid automatic control loop is defined on the basis of the reference potential $V_{ref}$. Where, therefore, the automatic control loop is allowed to have a sufficient transfer function insofar as said control loop can be rendered stable, then the voltage of the video signal E12 is always set at a prescribed level corresponding to the reference potential $V_{ref}$. In other words, the voltage of the video signal E12 is always set at a substantially fixed level, regardless of the deterioration (changes with time) of the lamp 21b, variations in the sensitivity of the image pickup tube 30 caused, for example, by changes in ambient temperature, and changes in the distance between the foreground subject 17 and the distal end portion 14 of the endoscope. This fact means that an optical image can be projected on the target plane 30a of the image pickup tube 30 with a substantially stabilized brightness, thereby assuring the production of a video signal E12 having a high S/N ratio.

Figure 3:
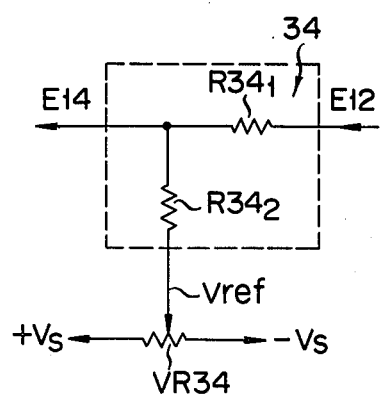
FIG. 3 is a concrete circuit arrangement of a comparator used with the image pickup apparatus of FIG. 1.

FIG. 3 shows the concrete arrangement of the comparator 34 included in FIG. 1. The video signal E12 is supplied to a slider of a variable resistor VR34 through resistors R34₁ and R34₂. Both ends of the variable resistor 34 are impressed with a positive potential $+V_S$ and a negative potential $-V_S$. The reference potential $V_{ref}$ is drawn out of the slider of the variable resistor VR34. The first signal E14 is sent forth from the junction of the resistors R34₁ and R34₂.

Figure 4:
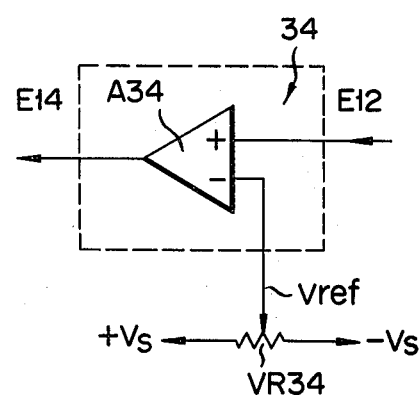
FIGS. 4 and 5 are modifications of FIG. 3.
Figure 5:
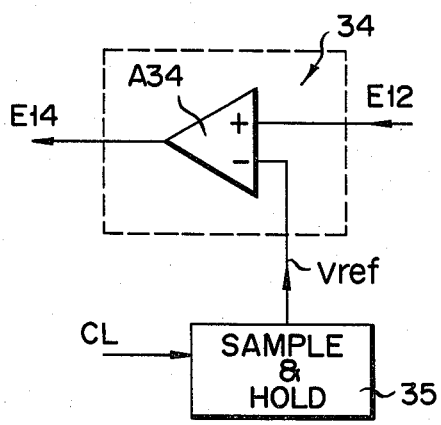

FIGS. 4 and 5 are modifications of FIG. 3. The video signal E12 is supplied to the non-inverted input terminal of an operational amplifier A34. The reference potential $V_{ref}$ is supplied to the inverted input terminal of said operational amplifier A34. In FIG. 4, the reference potential $V_{ref}$ is drawn out from the slider of the variable resistor VR34 as in FIG. 3. Referring to FIG. 5, the clamp pulse CL is sampled and held in a sample/hold cicuit 35 when a horizontal synchronizing pulse is issued, thereby producing a reference potential $V_{ref}$ corresponding to the clamp pulse CL.

Figure 6:
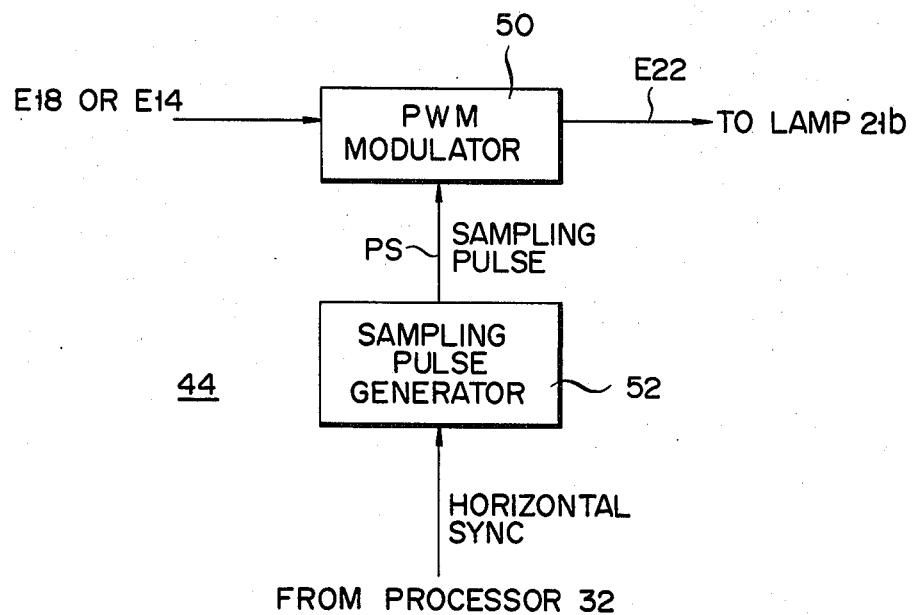
FIG. 6 is a modification of FIG. 1.

FIG. 6 is a modification of the feedback means 44 of FIG. 1. FIG. 6 represents the application of a conventional PWM or PCM modulator 50 which is supplied with the signal E18 or E14 corresponding to the video signal E12. The horizontal synchronizing pulse used in the processor 32 is delivered to a sampling pulse generator 52, which may be formed of a frequency multiplier or frequency divider. This sampling pulse generator 52 issues a sampling pulse PS upon receipt of the horizontal synchronizing pulse. The sampling pulse PS is supplied to the above-mentioned modulator 50, which produces a drive signal E22 having a duty cycle corresponding to the DC level of the signal E18 which is supplied to said modulator 50.

The brightness of the lamp 21b averaged in terms of time is substantially proportional to the duty cycle of said drive signal E22. The lamp 21b is intermittently operated in a timing synchronized with the horizontal scanning. The lamp 21b has such a heat capacity that even while the drive signal E22 is not issued, light emission is continued. Further visual persistence takes place in the image pickup tube. It is seen from the above-mentioned facts that if the modulator 50 carries out sampling at a properly selected rate, then the occurrence of a horizontal noise bar on the video image-reproducing screen can be practically suppressed. The modulator 50 which is only intermittently operated releases less heat than the amplifier 42 of FIG. 1, namely, consumes less power.

It will be noted that the embodiment described in the specification and illustrated in the accompanying drawings does not limit the scope of this invention in any way. In other words, the invention can be practiced with various additions and modifications without departing from the spirit and object of the invention and within the scope of the patent claims. For instance, it is possible to supply fixed power to the lamp 21b, provide an iris mechanism between the lamp 21b and light guide fiber bundle 20, and control the extent of operation of said iris mechanism in accordance with the drive signal E22. An image pickup apparatus embodying this invention can be used with an endoscope set forth in Japanese patent applications Nos. 158,869/78 and 158,870/78, filed by the same assignee as that of the present patent application. Further, the image pickup apparatus of this invention allows for the application of "IRIS SERVO APPARATUS" disclosed in Japanese patent application No. 56,867/80, filed by the same assignee. In other words, it is possible to use with the image pickup apparatus of the present invention a second automatic level control system (as set forth in the above-mentioned IRIS SERVO APPARATUS) which is actuated when the automatic level control system shwon in FIG. 1 of the present patent application is saturated.

What is claimed is:

1. An image pickup apparatus which comprises:
   light source means for providing an illumination light;
   an endoscope including illumination means coupled to said light source means for transmitting the illumination light from said light source means to a foreground subject to be illuminated; and image transmission means for sensing an optical image of the foreground subject illuminated by said illumination means and for transmitting the optical image;
   image signal conversion means coupled to said image transmission means of said endoscope for converting the optical image into a video signal;
   clamp means coupled to said image signal conversion means for clamping the black level of said video signal to provide a clamped signal; and
   integrator means coupled to said clamp means and to said light source means for integrating said clamped signal to continuously provide averaged information of said video signal to said light source means to continuously set the amount of illumination light provided by said light source means in accordance with said averaged information;
   said light source means, illumination means, image transmission means, image signal conversion means, clamp means and integrator means jointly comprising an automatic level control loop which is continuously actuated so at to continuously set amount of illumination light in accordance with said averaged information to cause said video signal to be at a substantially constant prescribed level;
   said automatic level control loop further comprising comparator means coupling said image signal conversion means to said clamp means for comparing the level of the video signal with that of a reference potential and for generating an output signal when the video signal reaches a level corresponding to the reference pontential; and
   said clamp means clamping said output signal of said comparator means at a prescribed level and at a predetermined timing.

2. The image pickup apparatus of claim 1, wherein said light source means includes means for varying the intensity of the light emitted from said light source means in accordance with said averaged information of said video signal.

3. The image pickup apparatus of claim 1, wherein said automatic level control loop further comprises means coupled to said clamp means for supplying said reference potential to said comparator means in response to a clamp pulse issued by said clamp means in a prescribed timing.

4. The image pickup apparatus of claim 3, wherein said image signal conversion means includes means for generating a horizontal synchronizing signal; and the clamp pulse is issued in a timing synchronized with said horizontal synchronizing signal.

5. The image pickup apparatus of any one of claims 1, 3 or 4, wherein said endoscope includes a flexible tube; and said illumination means and image transmission means comprise an optical fiber bundle extending through said flexible tube of said endoscope.

* * * * *

UNITED STATES PATENT AND TRADEMARK OFFICE
CERTIFICATE OF CORRECTION

PATENT NO. : 4,423,436

DATED : December 27, 1983

INVENTOR(S) : Kenji KIMURA

It is certified that error appears in the above-identified patent and that said Letters Patent is hereby corrected as shown below:

On the initial page of the patent, In the Abstract,
lines 13 and 14, change "illumination fiber,
optics image fiber," to --illumination fiber
optics, image fiber optics,--.

Signed and Sealed this

Eighteenth Day of September 1984

[SEAL]

Attest:

GERALD J. MOSSINGHOFF

Attesting Officer  Commissioner of Patents and Trademarks